United States Patent [19]

Fudenberg

[11] Patent Number: 4,801,533

[45] Date of Patent: Jan. 31, 1989

[54] METHOD OF USING ALPHA-1 ACID GLYCOPROTEIN ON T-CELLS AS A MARKER FOR ALZHEIMER'S DISEASE

[76] Inventor: H. Hugh Fudenberg, P.O Box 702, Sullivan Island, S.C. 29482

[21] Appl. No.: 878,352

[22] Filed: Jun. 25, 1986

[51] Int. Cl.$^4$ ............................................. G01N 33/53
[52] U.S. Cl. ........................................ 435/7; 436/501; 436/504; 436/518; 436/536; 436/538; 436/542; 436/547; 436/815; 436/811
[58] Field of Search .................... 435/7; 436/501, 504, 436/518, 536, 538, 542, 547, 815, 811

[56] References Cited

U.S. PATENT DOCUMENTS 4,728,605  3/1988  Fudenberg et al. ................ 436/811

Primary Examiner—Robert J. Warden
Assistant Examiner—Stephen C. Wieder
Attorney, Agent, or Firm—Iver P. Cooper

[57] ABSTRACT

Alzheimer's Disease (AD) sufferers may be diagnosed by examination of T-cells from their peripheral blood. AD is marked by increased appearance of alpha-1 acid glycoprotein (AGP) on the surface of such cells. Among AD subjects normal for AGP, a subpopoulation exists which show elevated AMLR response as compared to age-matched controls. These tests may be used to diagnose AD or to screen possible therapeutic agents.

8 Claims, 2 Drawing Sheets

METHOD OF USING ALPHA-1 ACID GLYCOPROTEIN ON T-CELLS AS A MARKER FOR ALZHEIMER'S DISEASE

Until recently the manifestations of cerebral senility have been thought to result from arteriosclerosis with a subsequent diminution of adequate oxygen delivery to the nervous tissue, Terry, Ann. Rev. Neurosci. 3:77 (1980). However, it is now apparent that (in at least some individuals' central nervous systems) cerebral "aging" (loss of cognitive function) is due to primary degenerative functional deficiencies in the neural cells (neurons) themselves, Whitehouse, Science, 215:1237 (1982). These deficiencies, when so severe as to merit being categorized separately due to the severe defect in recent memory recall and cognitive function, are termed Alzheimer's syndrome, Katzman, Arch. Neurol., 33:217 (1976). In dementia of the Alzheimer's type, also referred to as Alzheimer's disease (AD), neuropathological brain examinations in most but not all patients have revealed some characteristic abnormalities, e.g., neuritic plaques, abnormal neurites, neurofibrillary tangles containing paired helical filaments composed of cross-linked polypeptides, that are especially prominent in the cerebral cortex and hippocampal formation, Perry, J. Neurol. Sci., 34:247 (1977). In the last decade, it has been found that excessive nerve cell loss occurs in the frontal and temporal cortices of the cerebral cortex. Recently, it has been demonstrated that there seems to be a relatively specific loss (75 percent) of the neurons in the basal nucleus of Meynert, Coyle, Science, 219:1184 (1983). The cells affected are the major source of extrinsic cholinergic input into the cortex.

A recent article by Goldsmith, "Attempts to Vanquish Alzheimer's Disease Intensify, Take New Paths," refers to AD as a "dementing disorder for which the diagnosis is unequivocal only post-mortem, the therapy almost non-existent, and prognosis grim." JAMA 251:1805 (Apr. 13, 1984).

Presently, AD is generally diagnosed on the basis of behavioral symptoms and psychological scoring. The diagnosis may be reinforced by morphological examination of the brain (by noninvasive methods like CAT scan) for structural abnormalities (frontal lobe cortical atrophy). In addition, biochemical examination of cerebrospinal fluid may reveal depressed levels of the enzymes choline acetyltransferase and/or acetylcholine esterase. After death, the presence of AD may be established unequivocally by the detection of atrophy of the basal nucleus of Meynert.

Naturally, it is desirable to diagnose AD prior to death. My related application, Ser. No. 636, 287, filed July 31, 1984, describes one method of diagnosing AD. This application describes another.

My novel diagnostic method is based in part on the recognition of the presence of alpha-1-acid glycoprotein (AGP) (orosomucoid) on the membrane of T Cells. AGP is a component of normal serum which is elevated during acute inflammation, cancer, and pregnancy. Exogenous AGP, when added to lymphocyte cultures, is known to affect mitogenesis, cytotoxic reaction, antibody secretion, and binding of sheet erythrocytes. Chiu, et al., *Immunology*, 32:997 (1977); Bennett, et al., *PNAs*, 77:6109 (1980); Cheresh, et al., *Immunology*, 68:779 (1984); and Cheresh, et al., *Immunology*, 51:541 (1984).

The autologous mixed leucocyte reaction (AMLR) is thought to provide a valuable model for investigation of the processes by which T cells regulate immune responses, and particularly, of immunological communication between T and non-T cells. Weksler, et al., *Adv. Immunol.*, 31:271 (1981).

Leonardi, Caria, Arata, DiGeronimo, Canonica and Fudenberg, in *Clinical Immunology and Immunopathology*, 39:121 (1986), note that lymphocytes from AD patients show a consistently higher AMLR response than in age-matched controls. The paper is generally directed to T-Lymphocyte functional impairment in Huntington's Disease. (In HD, the AMLR response is lower than in age matched controls.)

SUMMARY OF THE INVENTION

Alzheimer's disease may be diagnosed by analysis of the blood of suspect individuals for (1) the percentage of T-cells with surface membrane alpha-1 acid glycoprotein (AGP) or (2) radiolabeled thymidine uptake by T-cells activated by non-T peripheral blood mononuclear cells. Approximately 90% of AD patients have elevated levels of T-cells with surface AGP as compared to aged matched controls. Of the 10% who score as normal on the AGP test, half will show elevated thymidine uptake (for DNA Synthesis) by T-cells activated by non-T peripheral blood mononuclear cells in the so-called autologous mixed leucocyte reaction (AMLR). Thus, 95% of AD sufferers will be identified by one or both of these tests.

In addition, possible therapeutic agents may be evaluated in vitro by "before" and "after" studies of T cells from known AD patients for surface AGP expression and AMLR response. Agents which normalized these T cell characteristics would be prime candidates for in vivo testing.

Other advantages of the present invention will be evident to those skilled in the art after consideration of this specification.

DETAILED DESCRIPTION OF THE INVENTION

Selection of AD Subjects

Figure 1:
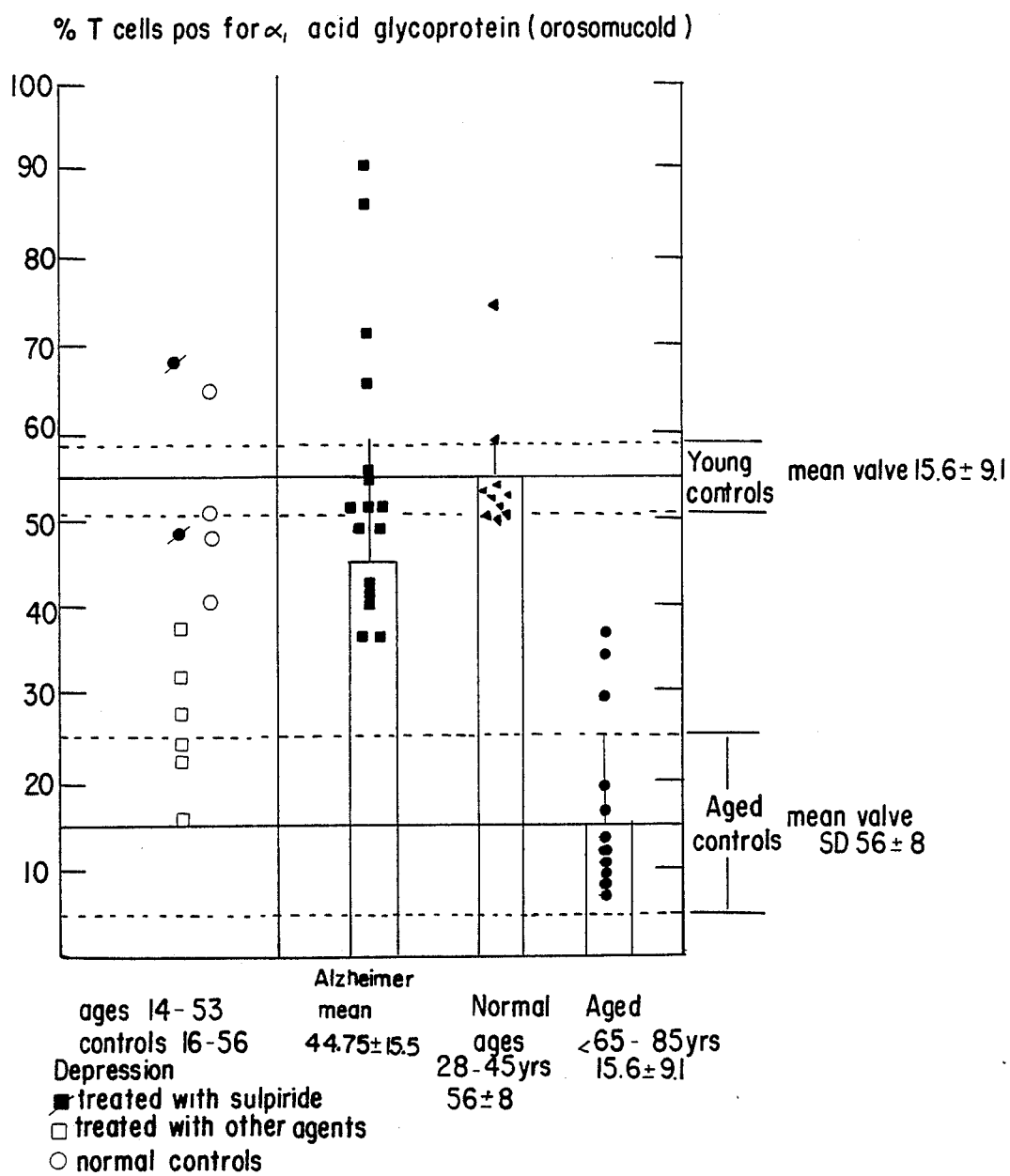
FIG. 1 presents the results of an assay of peripheral T cells bearing surface alpha-1acid glycoprotein in young controls, aged controls, and AD subjects.

Candidates must have a history of two years of progressively worsening symptoms characteristic of AD. See Reisberg, et al, The Global Deterioration Scale (GDS) for Assessemnt of Primary Degenerative Dementia, Am.J. Psychiat., 139:1136 (1982). A CAT scan must show cortical atrophy, but no other abnormalities (e.g., brain tumors). The subject should have normal thyroid and vitamin B functions, should be negative serologically for syphilis, and should exhibit diffuse, nonspecific abnormalities on an electroencephalogram.

Isolation and Fractionation of Mononuclear Cells

Mononuclear cells (MNC) were isolated from 40 ml of heparinized peripheral blood as described by Direnzo, et al., Ann. Allergy, 53:272 (1984), using a Ficoll-Hypaque density gradient (Pharmacia, Piscataway, NJ) (20 min, 1800 rpm). The cells were then washed three times in RPMI-1640 medium (Gibco, Chagrin Falls, OH) (10 min, 1500 rpm). T and non-T cells were separated by E-rosette formation. Briefly, MNC ($5 \times 10^6$/ml in RPMI-1640 with 5% fetal calf serum (FCS) (Hyclone Lab, Logan, UT) were centrifuged (5 min, 1000 rpm) in the presence of a 10% solution of 2 aminoethylisothio-ozonium bromide hydrobromide (AET)-treated sheep red blood cells (SRBC) (Chisolm Biological Laboratory, Seabrook, SC) (1:4 AET-treated sheep red blood cells to MNC suspension) and kept at 4° C. for at least one hr. E-rosette forming cells were then separated from non-rosetting cells on a Ficoll-Hypaque gradient (20 min, 1800 rpm). The pellet was gently resuspended and layered on top of a second Ficoll-Hypaque gradient. The SRBC on the T-cell pellet obtained were then removed by lysis with distilled water. The band containing non-T cells was obtained by the same procedure. The T and non-T lymphocytes were then washed three times using RPMI-1640 and resuspended at a concentration of $2 \times 10^6$/mi.

Immunofluorescence

First, a preparation of Ig fraction of rabbit anti-human $a_1$-AGP (1:50) (Dako, Westbury, NY) was reacted (30 min, 4° C.) with T-cells isolated as set forth above.

Next, (30 min, 4° C.) fluoresceinated goat anti-rabbit (1:50) antibody was reacted (30 min, 4° C.) with the AGP: antibody complex.

Culture Conditions for AMLR

Briefly, AMLR was performed as reported by Direnzo, et al. (1984): $3 \times 10^6$ responding T lymphocytes were mixed with $3 \times 10^6$ autologous non-t cells (including adherent cells) in a total volume of 3 ml. Culture medium was RPMI-1640 supplemented with 2 mM L-glutamine (1 ml per 100 ml), penicillin-streptomycin solution (1 ml per 100 ml medium; Gibco), and 5% FCS. Cultures containing $3 \times 10^6$ T lymphocytes with $3 \times 10^6$ autologous non T cells were formed in 3 ml complete medium RPMI-1640 and incubated three days in a 37° C. humidified 5% $CO_2$ atmosphere. After incubation, the T cells were isolated as previously described.

EXAMPLE 1

T cells from young controls, aged controls, and AD subjects were assayed for surface AGP. As shown in FIG. 1, aged controls (over 65) had a mean value of 15.6% positive T cells. AD subjects had a mean value of 44.75%, and young controls subjects a mean of 56%. It will be noted that only two AD subjects had AGP at levels within even the extreme range observed for normal aged controls.

EXAMPLE 2

Figure 2:
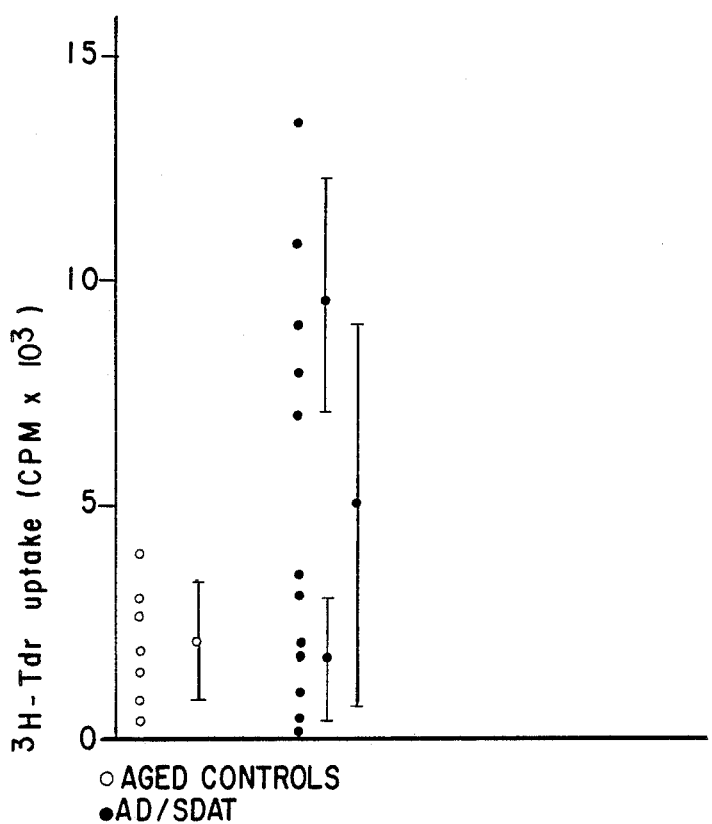
FIG. 2 shows $^3$H-Tdr uptake by T cells stimulated by AMLR in aged controls and AD patients.

T cells from AD Patients and Aged controls were assayed for thymidine uptake after an AMLR reaction. Aged controls all had values under 5,000 cpm. AD patients fell into two subsets, one comparable to the aged controls, and the other having elevated values, as shown in FIG. 2.

While the AGP assay set forth above is an immunofluorescent assay, it will be understood that RIA, EIA and other assay techniques capable of determining surface membrane alpha-1 acid glycoprotein might also be employed. Use of fluorescence-activated cell sorters is also of interest.

Though the stimulation of T-cells in an AMLR is conventionally determined by measuring thymidine uptake (which is related to the rate of DNA synthesis), the invention is not so limited. The non-T cells which may be employed in the AMLR include B cells and monocytes.

The use of the AMLR assay is in conjunction with the AGP assay is preferred, but not essential.

The Examples given herein are intended to illustrate, and not to limit the invention.

I claim:

1. A method of diagnosing a dementia of the Alzheimer's type characterized by a change in the percentage of T-cells bearing surface membrane alpha-1 acid glycoprotein which comprises providing T-cells from a subject, determining the percentage of those T cells which bear surface membrane alpha-1 acid glycoprotein, and comparing that percentage of the percentage of T cells which bear said glycoprotein in a control, whereby said dementia is diagnosed.

2. The method of claim 1, wherein the T cells are exposed to an antibody against alpha-1 acid glycoprotein, and the formation of the antigen-antibody complex is detected.

3. The method of claim 2 in which the antigen is detected by immunofluorescence.

4. The method of claim 2 in which a labeled anti-antibody is reacted with the antigen-antibody complex, unbound anti-antibody is separated, and the bound anti-antibody is detected.

5. The method of claim 4 in which the anti-antibody bears a fluorescent label.

6. The method of claim 1, further comprising determining the degree of activation of said T cells by non-T peripheral blood mononuclear cells in an autologous mixed leukocyte reaction.

7. The method of claim 6 in which the degree of activation is determined by measuring the increase in thymidine uptake of said T cells as a result of said reaction.

8. A method of screening a potential therapeutic for AD which comprises providing T cells from an AD subject, said T cells being characterized by altered percentages of T cells bearing surface membrane alpha-1 acid glycoprotein relative to T cells from a normal subject, and determining the percentage of said T cells bearing surface membrane alpha-1-acid glycoprotein both before and after exposure to the therapeutic, a therapeutic for AD being selected on the basis of its ability to normalize said percentage.

* * * * *